(12) United States Patent
Serafin

(10) Patent No.: US 12,727,908 B2
(45) Date of Patent: Sep. 8, 2026

(54) SURGICAL TEMPLATE AND METHOD OF USE

(71) Applicant: Donald Serafin, Durham, NC (US)

(72) Inventor: Donald Serafin, Durham, NC (US)

(73) Assignee: Donald Serafin, Durham, NC (US)

( * ) Notice: Subject to any disclaimer, the term of this patent is extended or adjusted under 35 U.S.C. 154(b) by 0 days.

(21) Appl. No.: 18/416,495

(22) Filed: Jan. 18, 2024

(65) Prior Publication Data

US 2024/0245425 A1 Jul. 25, 2024

Related U.S. Application Data

(60) Provisional application No. 63/439,902, filed on Jan. 19, 2023.

(51) Int. Cl.
*A61B 17/3209* (2006.01)
*A61B 17/32* (2006.01)

(52) U.S. Cl.
CPC .................. *A61B 17/32093* (2013.01); *A61B 2017/320052* (2013.01)

(58) Field of Classification Search
CPC .......................................... A61B 2017/320052
See application file for complete search history.

(56) References Cited

U.S. PATENT DOCUMENTS 4,192,312 A * 3/1980 Wilson .................. A61B 17/32 128/853
4,576,163 A 3/1986 Bliss
4,886,079 A 12/1989 Mooney
4,944,737 A * 7/1990 Bloom .................. A61B 17/32 606/1
5,368,589 A 11/1994 Tovey et al.
6,626,865 B1 9/2003 Prisell
(Continued)

FOREIGN PATENT DOCUMENTS

| | | |
|---|---|---|
| CN | 111529085 | 8/2020 |
| CN | 212592465 | 2/2021 |
| YU | 20804 | 5/2006 |

OTHER PUBLICATIONS

Hon et al. "Rhomboid Flap" Atlas Oral Maxilofacial Surg Clin N Am 28 (2020) pp. 17-22 (Year: 2020).*
(Continued)

*Primary Examiner* — Elizabeth Houston
*Assistant Examiner* — Lindsey Bachman
(74) *Attorney, Agent, or Firm* — Business and IP Law; Todd M. Hess, Esq.

(57) ABSTRACT

A surgical template enables marking a pattern on skin to create a skin flap for closing an opening in the skin. The template is a planar sheet having an opening in the shape of a rhomboid. The sheet has a first pair of holes linearly spaced along an axis passing through opposed obtuse corners of the rhomboid. A second pair and a third pair of holes are spaced from the first pair of holes such that a line from adjacent holes of the first pair of holes to the second pair or third pair of holes is parallel to and equal in length to the adjacent side of the rhomboid. The edges of the sheet defining the opening mechanically guide a marker for marking excision lines. Each of the pairs of holes define axes therebetween for marking incision lines on the skin forming a pattern for the skin flap.

10 Claims, 16 Drawing Sheets

(56) References Cited

U.S. PATENT DOCUMENTS

| | | | | |
|---|---|---|---|---|
| 7,740,647 | B2 | 6/2010 | Mueller | |
| 7,752,768 | B2 * | 7/2010 | Young .................... | A61B 90/39<br>33/566 |
| 8,439,945 | B2 | 5/2013 | Belson et al. | |
| 8,709,069 | B2 | 4/2014 | Scholz et al. | |
| 9,226,798 | B2 | 1/2016 | Tripathi et al. | |
| 2007/0043323 | A1 | 2/2007 | Davey | |

OTHER PUBLICATIONS

Fee et al. (Rhomboid Flap Principles and Common Variations, The Laryngoscope, Nov. 1976, pp. 1706-1711) (Year: 1976).*

Sayadi, Lohrasb R. et al.; "A Novel Innovation for Surgical Flap Markings Using Projected Stencils", Plastic & Reconstructive Surgery, vol. 142 (3)—Sep. 1, 2018, Orange Calif.; Gainesville, Fla.; and Burlington, Vt.

Towend J.; "A Template for the Planning of Rhombic Skin Flaps", Plastic & Reconstructive Surgery, vol. 92, No. 55, Oct. 1993, Chichester, United Kingdom.

* cited by examiner

SURGICAL TEMPLATE AND METHOD OF USE

CROSS-REFERENCE TO RELATED APPLICATIONS

This application claims the benefit of U.S. Provisional Application No. 63/439,902, filed Jan. 19, 2023, the teaching of which is incorporated herein in its entirety by reference.

BACKGROUND

A surgical template and method of use in surgery are described and, more particularly, a surgical template and method of use for marking a pattern on skin prior to performing surgery to create a skin flap for closing an opening or wound in the skin.

Various surgical specialties are often confronted with difficult wounds requiring closure. In some cases, skin is removed along with a skin defect leaving a hole or opening in the skin that must be closed. When tissue approximation is not possible, skin closure requires that an adjacent flap of skin be moved to cover the wound opening or where the defect was removed. In this procedure, a flap of skin of the approximate size of the opening to be covered is moved from one location to another location. The donor tissue is obtained from the area of the skin adjacent to the defect and is not detached from the body, but merely moved while always remaining attached to other tissue.

There are many types and shapes of skin flaps for this skin closure procedure. One type is the rhomboid, or Limberg, flap. FIGS. 1A to 1E show a rhomboid flap procedure for a patient with a Mohs defect and failed rotation flap with components of a horizontal scar, a depressed segment and a vertical extension (See FIG. 2). The rhomboid flap is a versatile, random-pattern transposition flap that may be used almost anywhere on the skin, especially the head and neck. The rhomboid flap procedure requires considerable knowledge of geometry, skin biomechanics, and in the case of facial surgery, knowledge of facial anatomy combined with a sense of aesthetics and an appreciation for shapes, symmetry, and color.

The surgeon is presented with the problem of selecting the correct flap pattern for the closure. This typically requires some review of the technique and planning; however, unanticipated acute wound closure presentation does not afford such time. The sizing of the excision to produce the hole in the skin and the incisions to produce the flap need to be precise. Moreover, one can appreciate the difficulty in designing the rhomboid in the skin, constrained by the angles and equal lengths of the component lines. To compound the difficulty, the location of the wound or skin defect must be considered, as well as any alterations of existing adjacent structures during flap design.

For the foregoing reasons, there is a need for a template for aiding a surgeon in making proper sizes and shapes of excisions in an area of skin to be removed and the associated incisions for a corresponding flap to close the wound. The template should allow the surgeon to mark the skin for the incisions prior to the surgery for tissue removal and flap design. Ideally, the template will allow directly marking the skin surface leading to more precise, accurate and reliable incision patterns on the skin. The template should thus facilitate wound closure by straightforward design of the rhomboid skin flap rendering prior review unnecessary or when time is not practical.

SUMMARY

A surgical template is provided for marking a pattern on skin prior to performing surgery to create a skin flap for closing an opening or wound in the skin. The template comprises a substantially planar sheet having an opening defined by a continuous edge forming a closed geometric figure in substantially the shape of a rhomboid. The sheet has a first pair of holes linearly spaced along an axis passing through opposed obtuse corners of the rhomboid such that the distance between the corner of the rhomboid and the adjacent hole of the first pair of holes is equal to the length of the sides of the rhomboid. Each hole of a second pair and a third pair of holes is spaced from the first pair of holes such that a line from the adjacent hole of the first pair of holes to the adjacent one of the second pair or third pair of holes is parallel to and equal in length to the adjacent side of the rhomboid. The edges of the sheet defining the opening form a border for mechanically guiding a marker for marking excision lines on the skin surrounding the portion of skin intended to be removed. Each of the pairs of holes define axes therebetween for marking incision lines on the skin forming a pattern for the skin flap.

In one aspect, the sheet comprises a flexible, transparent material to conform to the skin. An inner surface of the sheet may be adhesive, which surface when applied against the skin causes the sheet to adhere to the skin.

In another aspect, the edges of the sheet defining the opening are configured for receiving at least a portion of a cutting edge of an incising instrument and for guiding the instrument during an incising of the tissue.

A method is also provided for marking a pattern on skin prior to performing surgery to create a skin flap for closing an opening or wound in the skin. The skin pattern marking method comprises the steps of providing a substantially planar sheet having an opening defining a closed geometric figure in substantially the shape of a rhomboid. The sheet has a first pair of holes linearly spaced along an axis passing through opposed obtuse corners of the rhomboid such that the distance between each obtuse corner of the rhomboid and the adjacent hole of the first pair of holes is equal to the length of the sides of the rhomboid. Each hole of a second pair and a third pair of holes is spaced from the first pair of holes hole such that a line from the adjacent hole of the first pair of holes to the adjacent one of the second pair or third pair of holes is parallel to and equal in length to the adjacent side of the rhomboid. The next steps include positioning the sheet on the skin, marking the skin along the edges of the sheet defining the opening for transferring the rhomboid pattern to the skin for use as excision lines for skin removal forming a hole in the skin, and marking dots on the skin through the holes for indicating an area from which to obtain the skin flap by drawing an incision line extending from the adjacent corner of the rhomboid opening and between the dots representing the incision to be made in the skin to produce the flap. The skin is then excised following the lines of the closed geometric figure marking for removing skin making a hole to be closed. An incision is made in the skin along the lines between the dots to produce a local flap to cover the hole in the skin.

In one aspect, the method further comprises the step of selecting a predetermined opening size from among a plurality of templates having different sizes of rhomboid-shaped openings.

In another aspect, the skin pattern marking method further comprises the step of selecting the orientation of the flap by rotating the template on the skin. The step of selecting the orientation of the flap may comprise identifying the line of maximum extensibility (LME) of the skin, aligning the template such that two sides of the rhomboid pattern are parallel to the LME, and aligning the short diagonal of the flap is parallel to the LME. In another aspect, the step of selecting the orientation of the flap comprises consideration of the relaxed skin tension line (RSTL) and the vector of tension (VOT) for anticipating distortion of adjacent tissues.

The skin pattern marking method may further comprise the step of cutting through the skin along the excision lines, and removing the patch of skin of rhomboid shape.

BRIEF DESCRIPTION OF THE DRAWINGS

For a more complete understanding of the surgical template and method, reference should now be had to the embodiments shown in the accompanying drawings and described below.

In the drawings.

DESCRIPTION

Figures 1A, 1B, 1C:
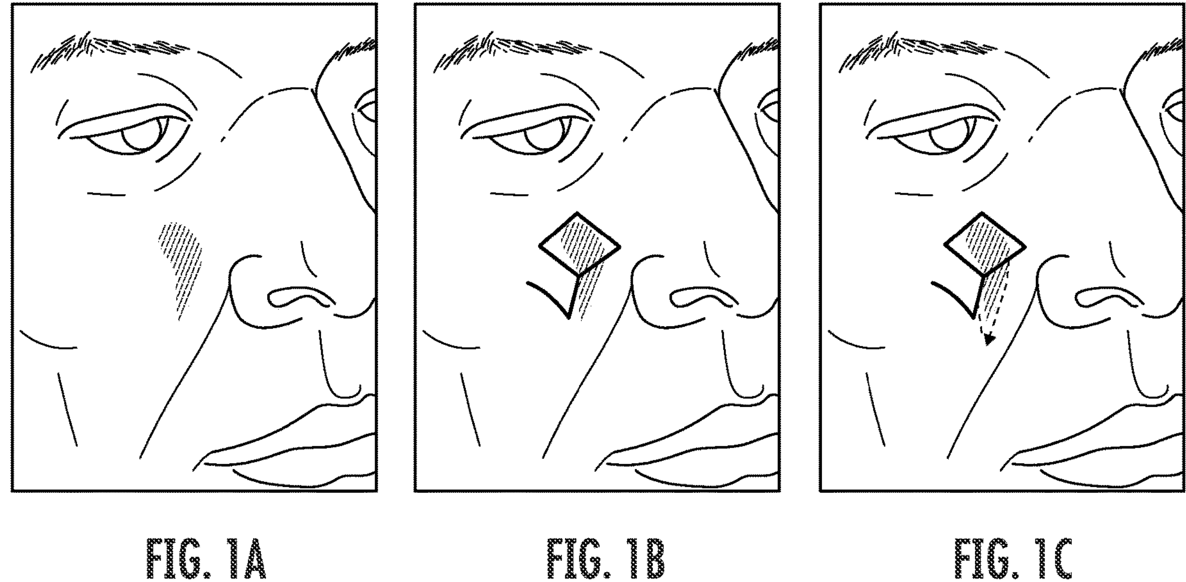
FIGS. 1A to 1E are perspective views showing a patient with a Mohs defect and failed rotation flap with components of a horizontal scar, a depressed segment and a vertical extension.
Figures 1D, 1E:
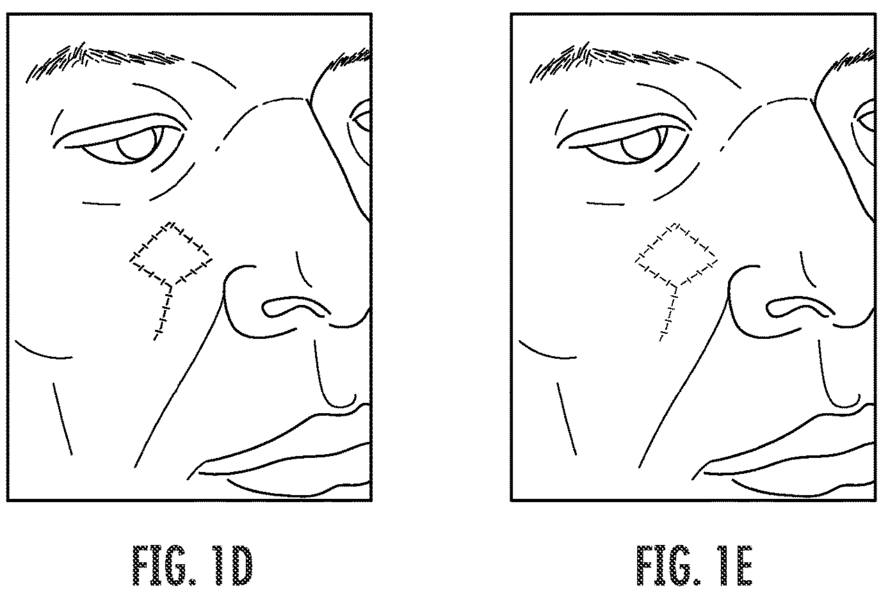
Figure 2:
FIG. 2 is a cut-away perspective view showing the patient including a scar component for the defect as shown in FIGS. 1A to 1E.

Referring now to the drawings, wherein like reference numbers refer to the same or similar elements throughout the several views, an embodiment of a surgical template is shown and generally designated at 20. The template 20 is designed to aid a surgeon in designing a rhomboid flap of skin for closure of a wound or skin lesion or defect. The template 20 is used to mark excision lines for forming an opening in the skin of predetermined shape and size. The template 20 also aids the surgeon in selecting and forming the corresponding skin flap to close the opening. The template 20 comprises a sheet 22 of material defining at least one opening 24 of a geometric figure and holes 26 or perforations for forming an outline of the skin flap. The opening 24 and related perforations 26 in the template 20 extend through the sheet material 22 and permit markings for intended excision lines and incision lines to be drawn on the skin prior to surgery. The template 20 when placed on the skin thus facilitates transfer of the excision pattern and flap design to the skin by marking.

A method is also provided for using the template 20 for marking the skin with the excision and incision patterns adjacent a wound, or skin defect or lesion for skin removal and flap surgery. The method comprises placing the template 20 on the skin followed by marking the excision and incision patterns onto the skin by tracing along one or more edges 28 of the shape defined by the opening 24 in the template 20. The related perforations 26 allow dots to be marked on the skin for indicating an area from which to obtain the skin flap.

The sheet material 22 forming the template 20 is generally rectangular. Notwithstanding the depicted embodiments, the general shape of the template 20 may be any shape such as a square, triangle, oval, circle, etc. The sheet 22 has two opposite large surfaces, a top surface 30 and an opposite bottom surface (not shown). The sheet 22 has at least one opening 24 having a shape defined by an outside perimeter edge 28. In one embodiment shown in the drawings, the shape or figure defined by the template 20 is a rhomboid which, together with the perforations 26, correspond to the excision and incision patterns for rhomboid flap surgery. The peripheral edge 28 circumscribes the opening 24 forming a continuous and uninterrupted edge within the template 20. The edge 28 serves as the guide for marking the area of the excision pattern on the skin that also represents the post operative position of the flap. It is understood that the template 20 may define an opening having any shaping suitable for marking the excision pattern.

The template 20 is preferably of a size large enough to cover at least an area sufficient to encompass desired excision and incision patterns. The overall size of the template 20 is preferably not so large as to cause it to be unwieldy during use. The depth or thickness of the sheet material 22 is small relative to its length and width. Additionally, the thickness of the sheet 22 is dependent upon the sheet material and not overly critical. The sheet 22 is preferably thick enough to withstand the handling associated with accurately marking the skin for multiple uses. Further, the sheet 22 is preferably thin enough to conform to the surface of the skin and not interfere with marking the incision patterns on the skin. For example, the thickness of a silicone or modified acrylic template is preferably no less than about 0.01 inches (0.254 millimeters) and no more than about 0.3 inches (0.762 millimeters). This thickness provides a template 20 that is resistant to cracking with good flexibility over a contoured surface.

The rhomboid-shaped opening 24 is a closed figure having four angles. Visually, the rhomboid appears as two equilateral triangles attached at a common base. At the location of attachment of the two triangles to form the rhomboid pattern, the angle is 120 degrees. Thus, the rhomboid pattern consists of four sides of equal length separated by two angles of 60 degrees and two angles of 120 degrees. The size of the rhomboid is determined by the length of the sides. By altering the length of the sides of a rhomboid design, the area within the design can be accurately altered. It will be understood particularly by those skilled in the art that there are other closed geometric figures which might be used which are sometimes designated as diamonds, triangles, circles, ellipses, and the like.

Figure 3:
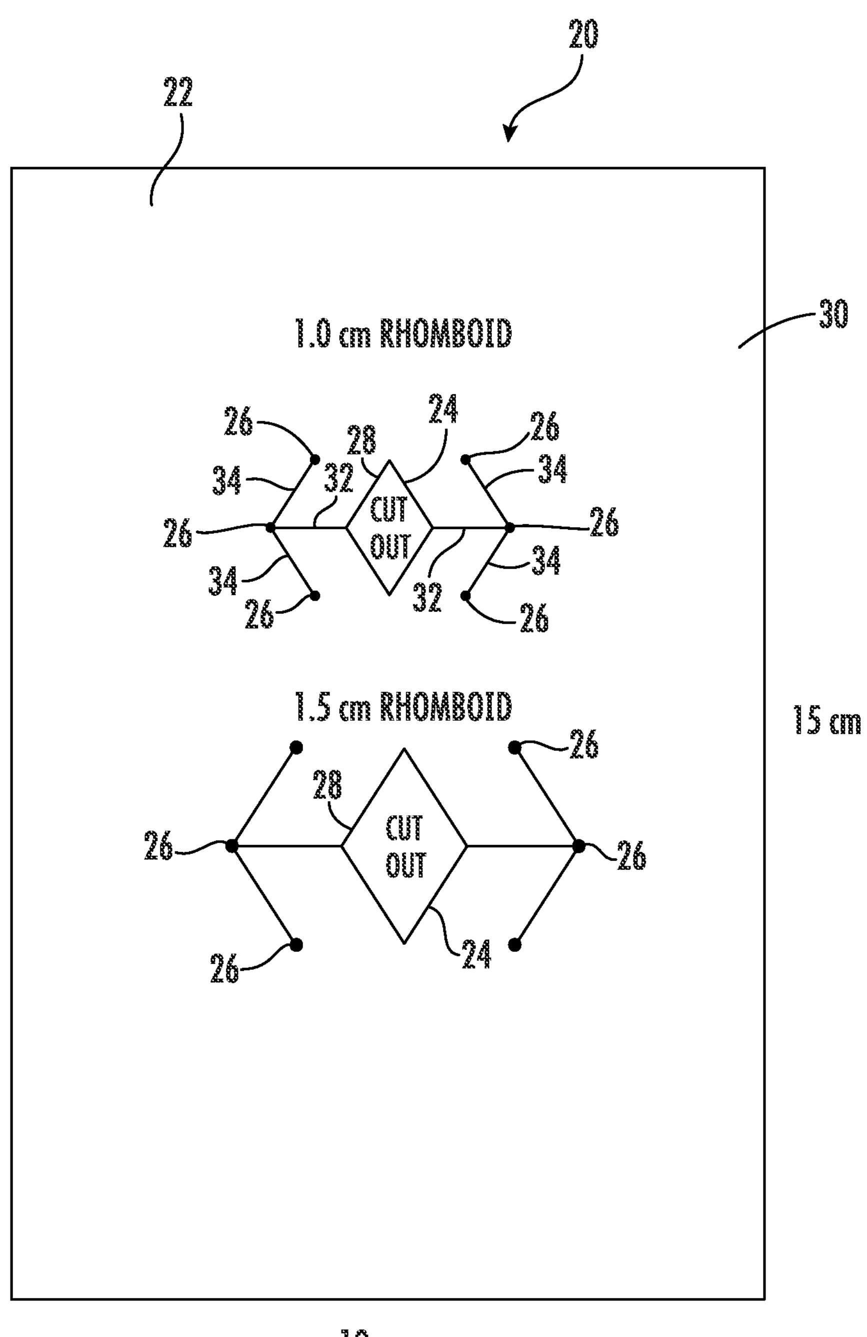
FIG. 3 is a top plan view of an embodiment of a template having two rhomboid patterns for designing a skin flap for closure of 1.0 cm and 1.5 cm wound openings or skin defects, respectively.
Figure 4:
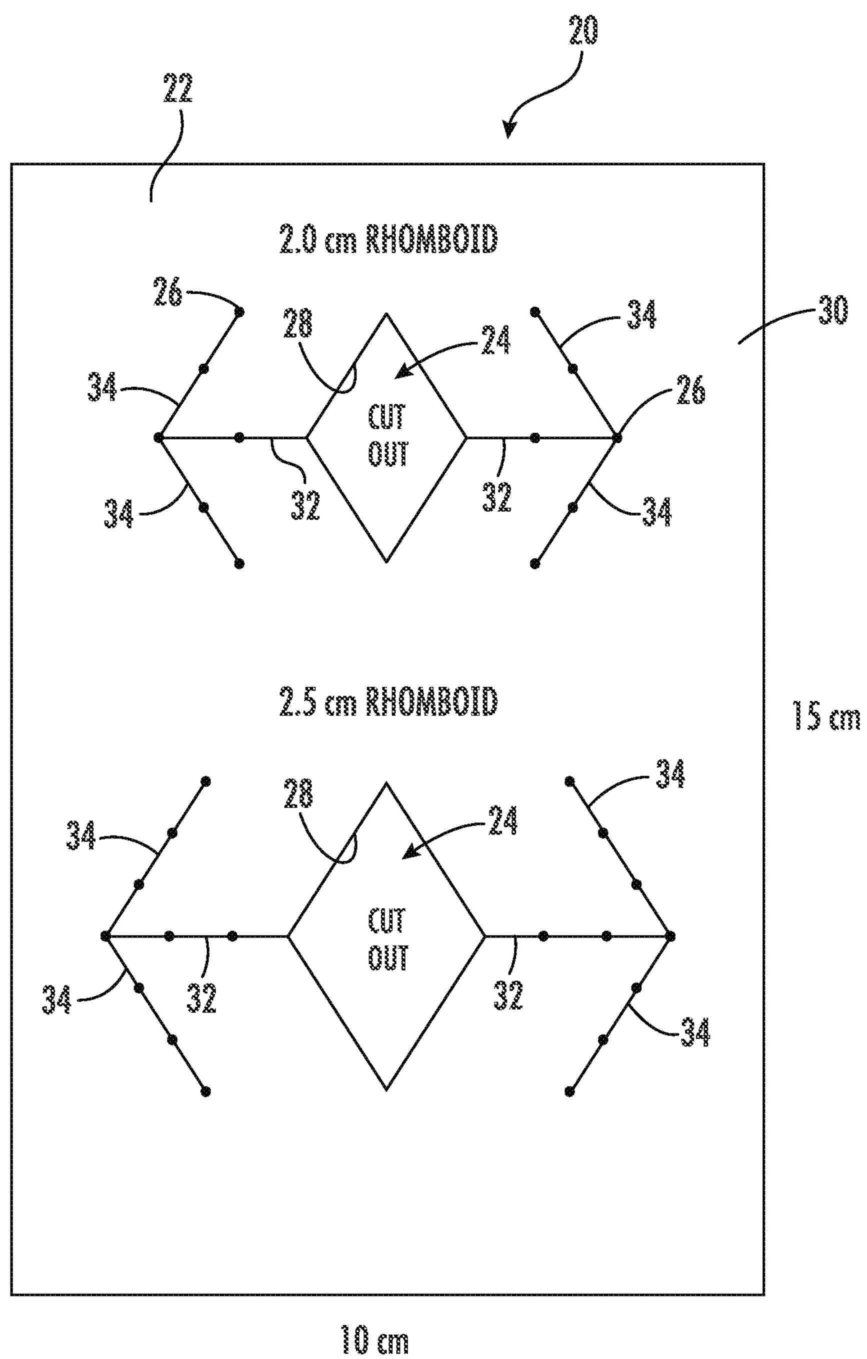
FIG. 4 is a top plan view of an embodiment of a template having two rhomboid patterns for designing a skin flap for closure of 2.0 cm and 2.5 cm wound openings or skin defects, respectively.
Figure 5:
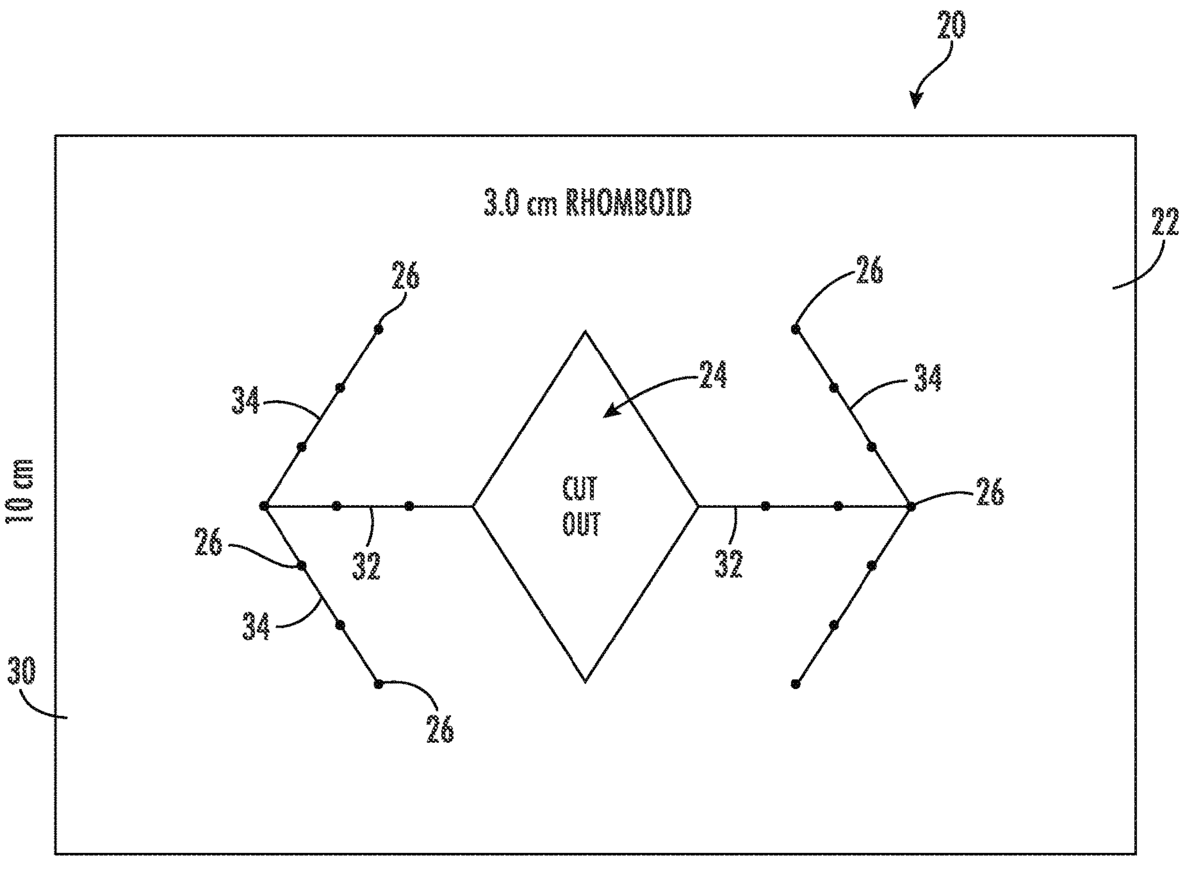
FIG. 5 is a top plan view of an embodiment of a template having a rhomboid pattern for designing a skin flap for closure of a 3.0 cm wound opening or skin defect.
Figure 6:
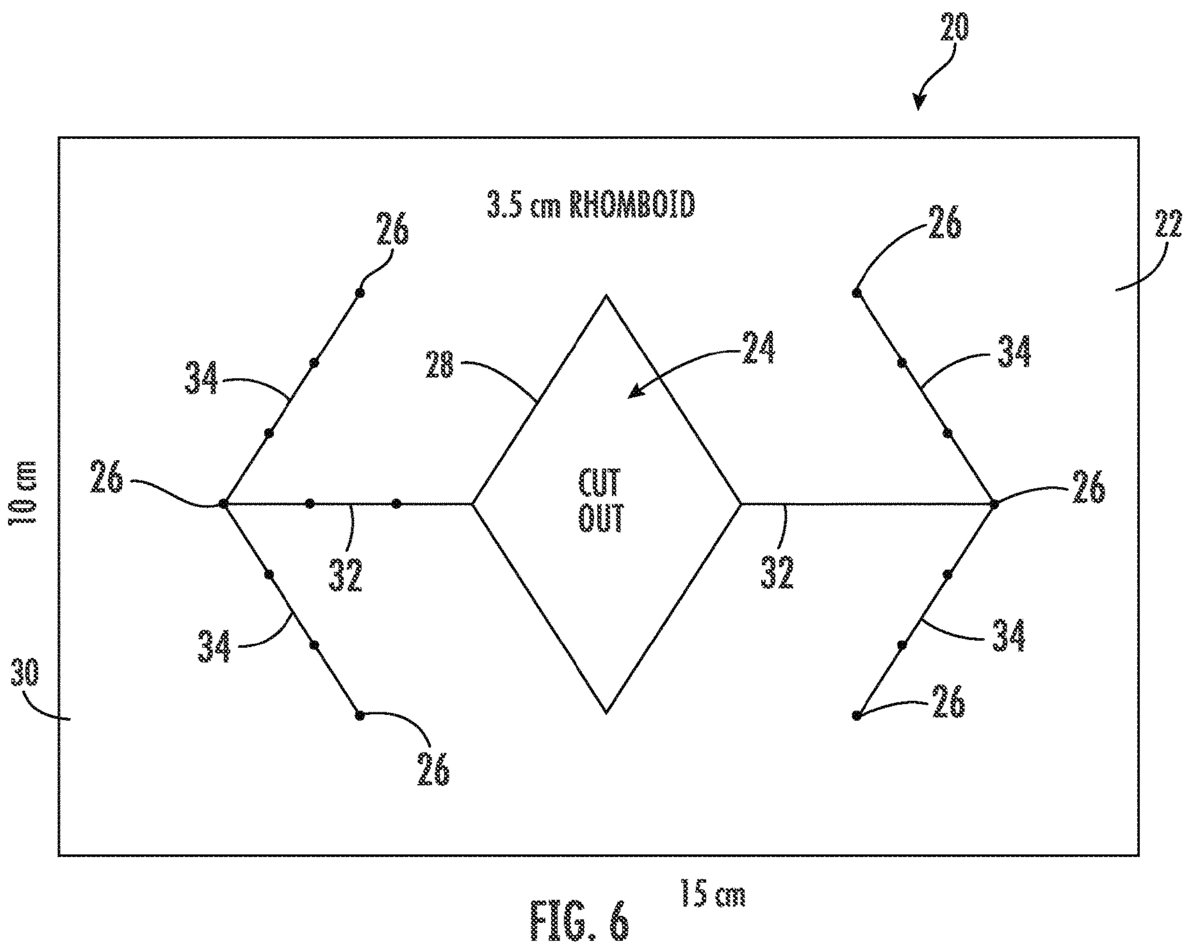
FIG. 6 is a top plan view of an embodiment of a template having a rhomboid pattern for designing a skin flap for closure of a 3.5 cm wound opening or skin defect.
Figure 7:
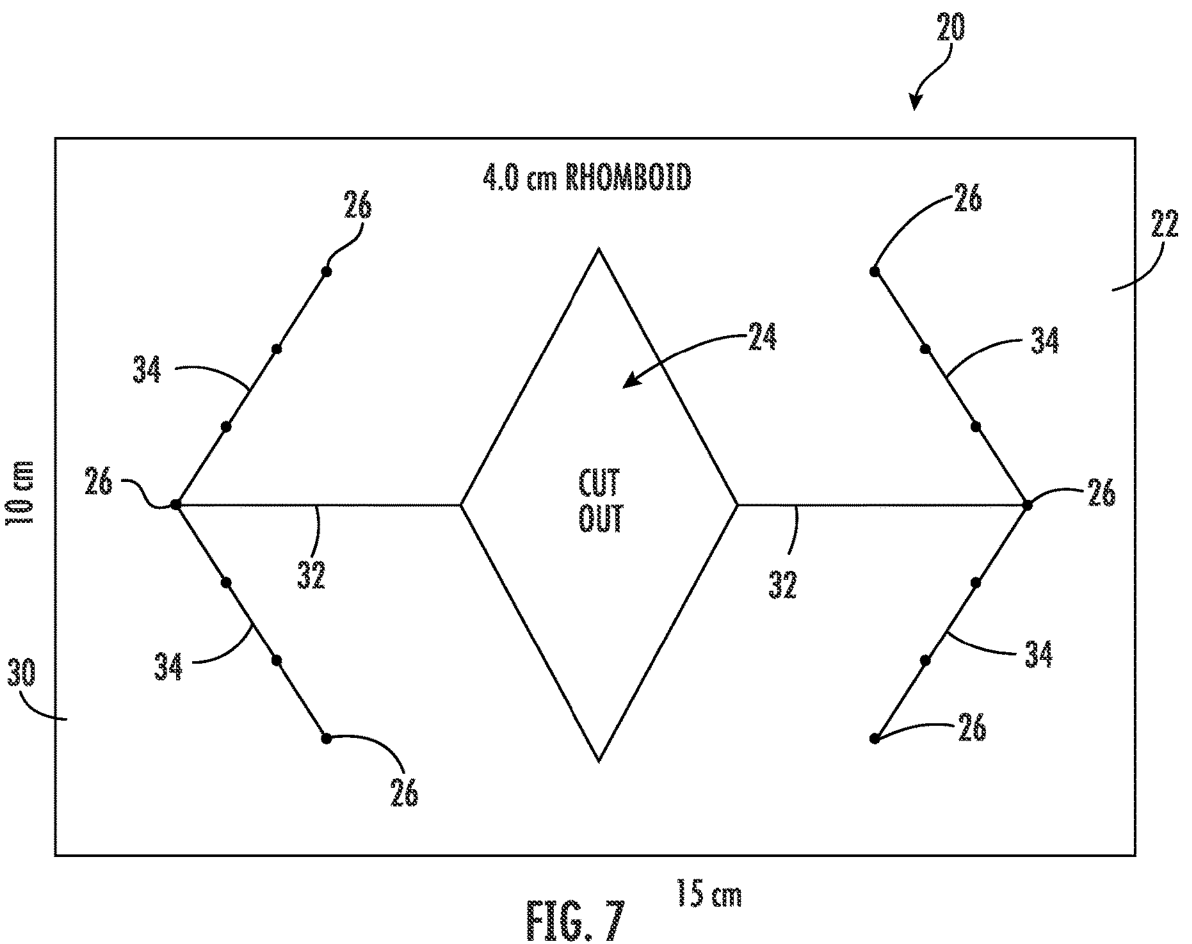
FIG. 7 is a top plan view of an embodiment of a template having a rhomboid pattern for designing a skin flap for closure of a 4.0 cm wound opening or skin defect.
Figure 8:
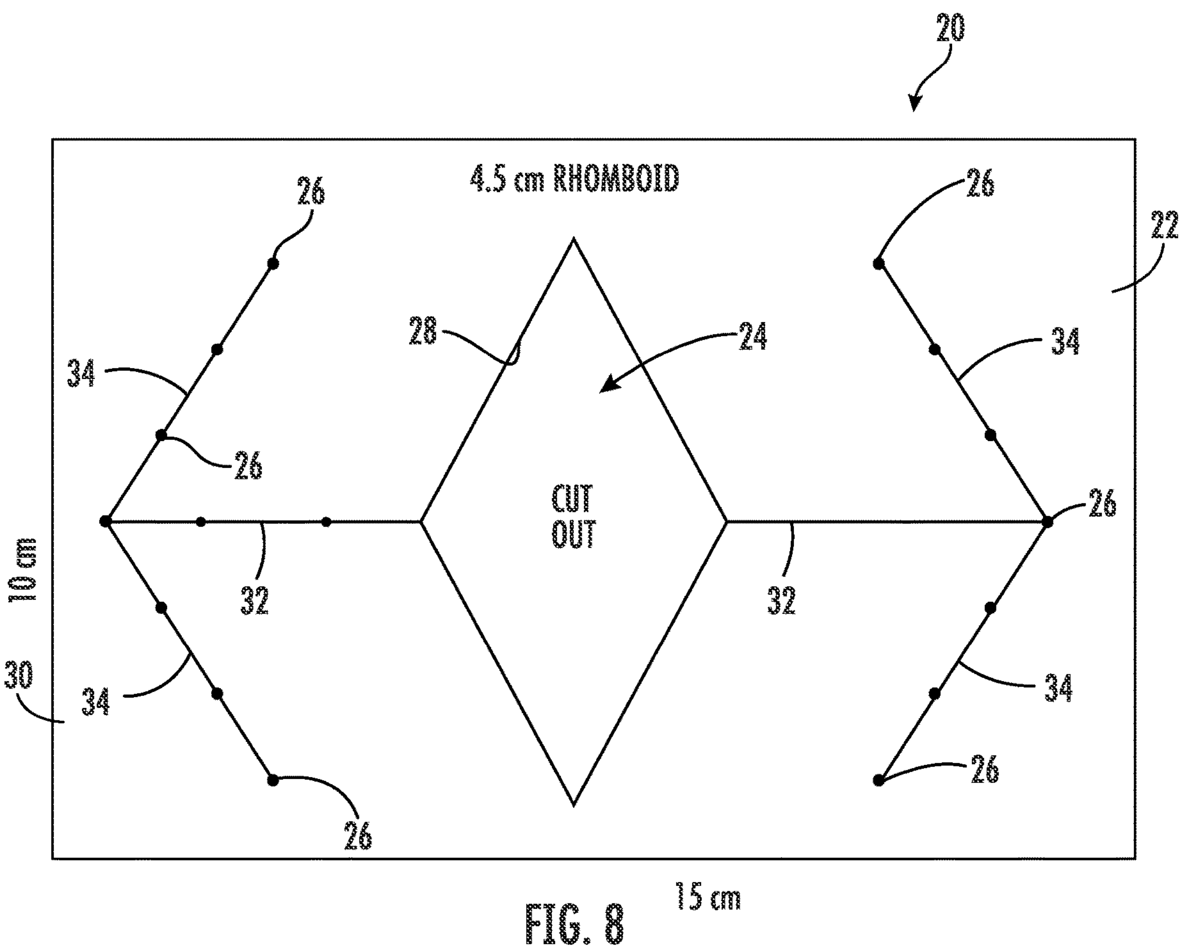
FIG. 8 is a top plan view of an embodiment of a template having a rhomboid pattern for designing a skin flap for closure of a 4.5 cm wound opening or skin defect.
Figure 9:
FIG. 9 is a top plan view of an embodiment of a template having a rhomboid pattern for designing a skin flap for closure of a 5.0 cm wound opening or skin defect.
Figure 9:
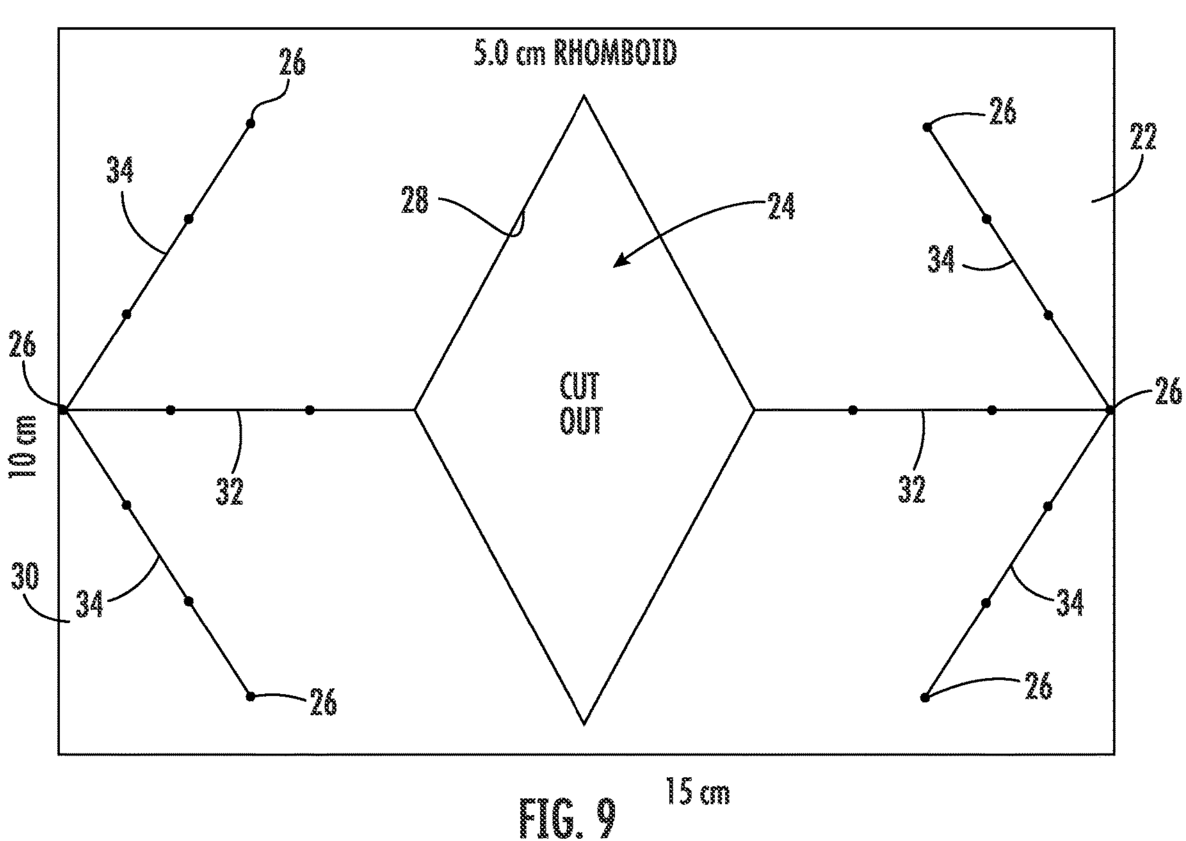
Figure 10A:
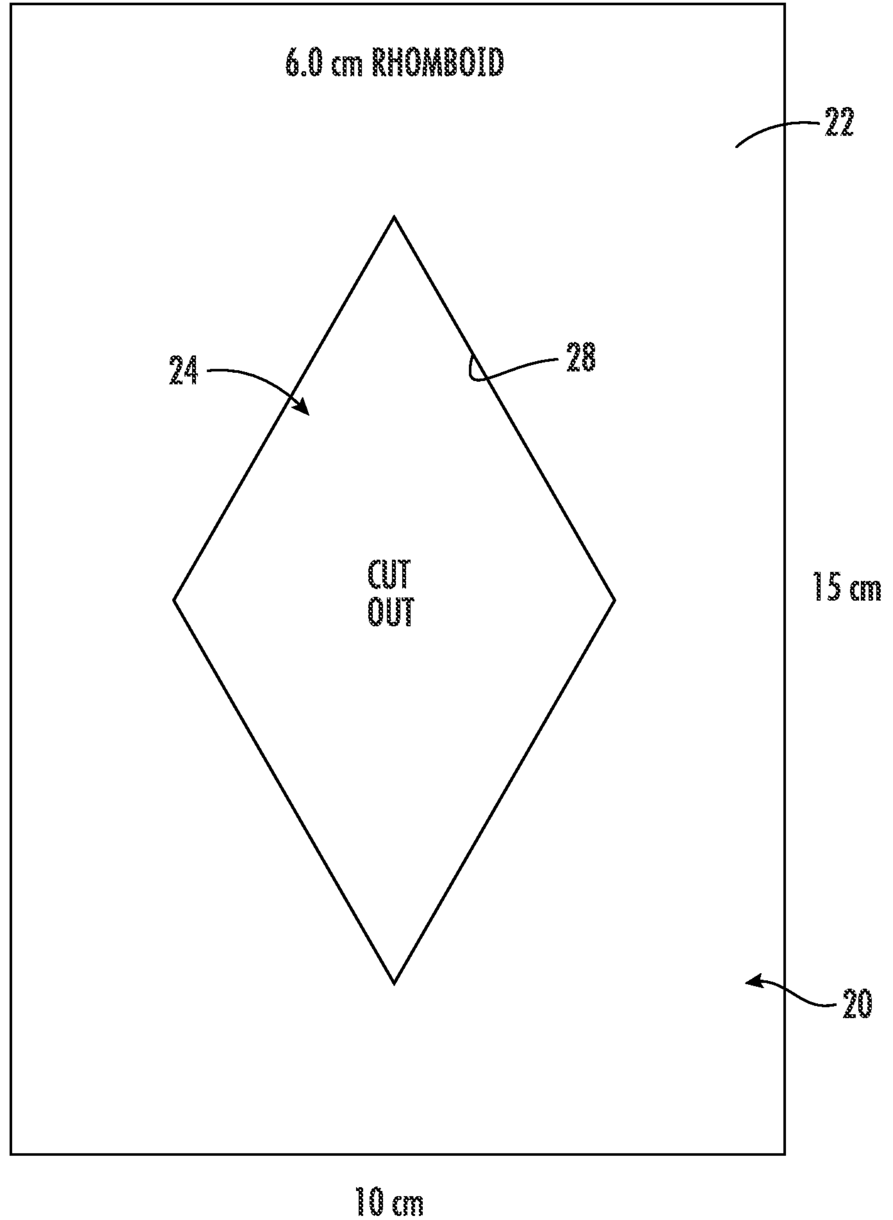
FIG. 10A is a top plan view of an embodiment of a first template having a rhomboid pattern for designing a skin flap for closure of a 6.0 cm wound opening or skin defect.
Figure 10B:
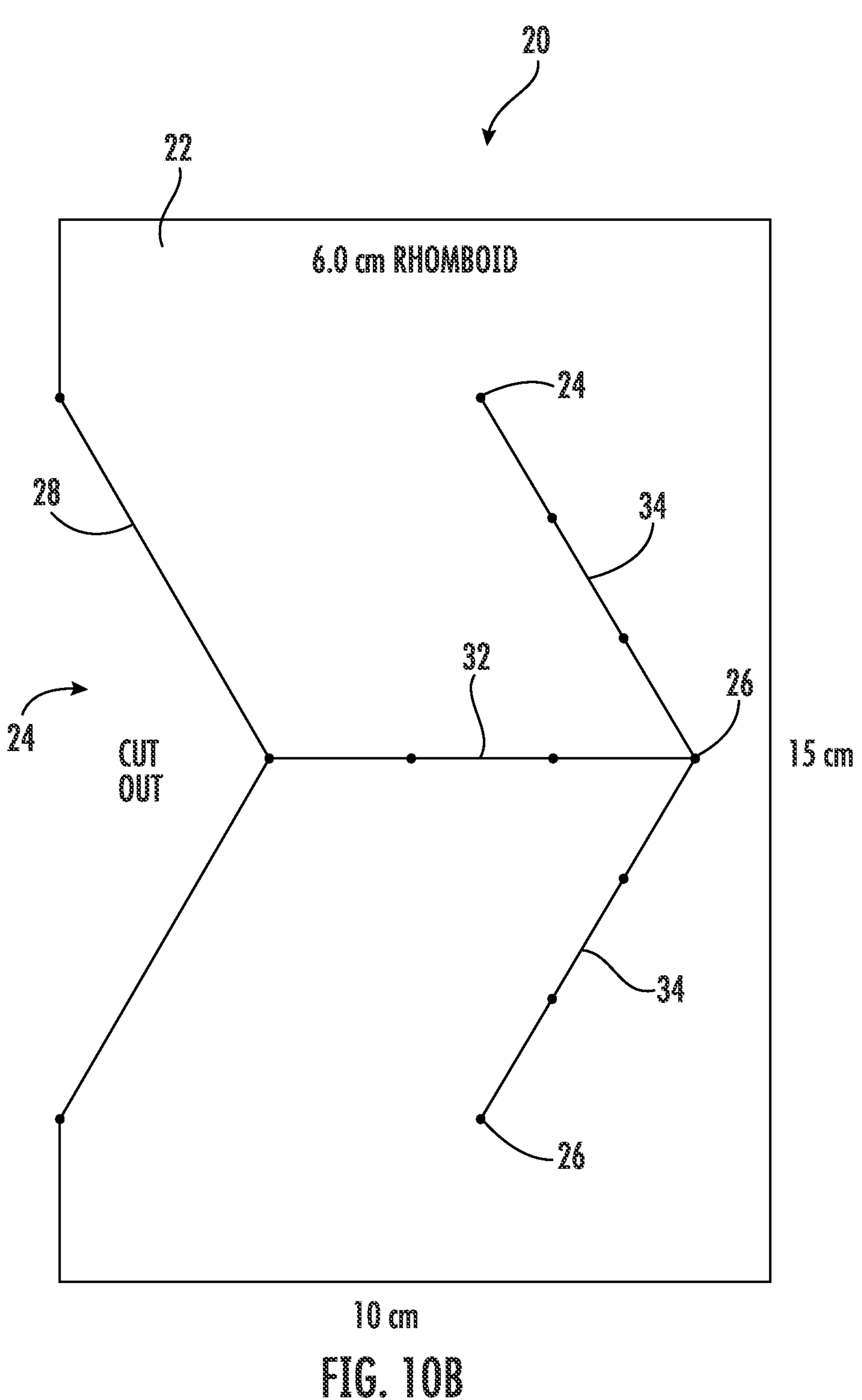
FIG. 10B is a top plan view of an embodiment of a second template having a rhomboid pattern for designing a skin flap for closure of a 6.0 cm wound opening or skin defect.
Figure 11A:
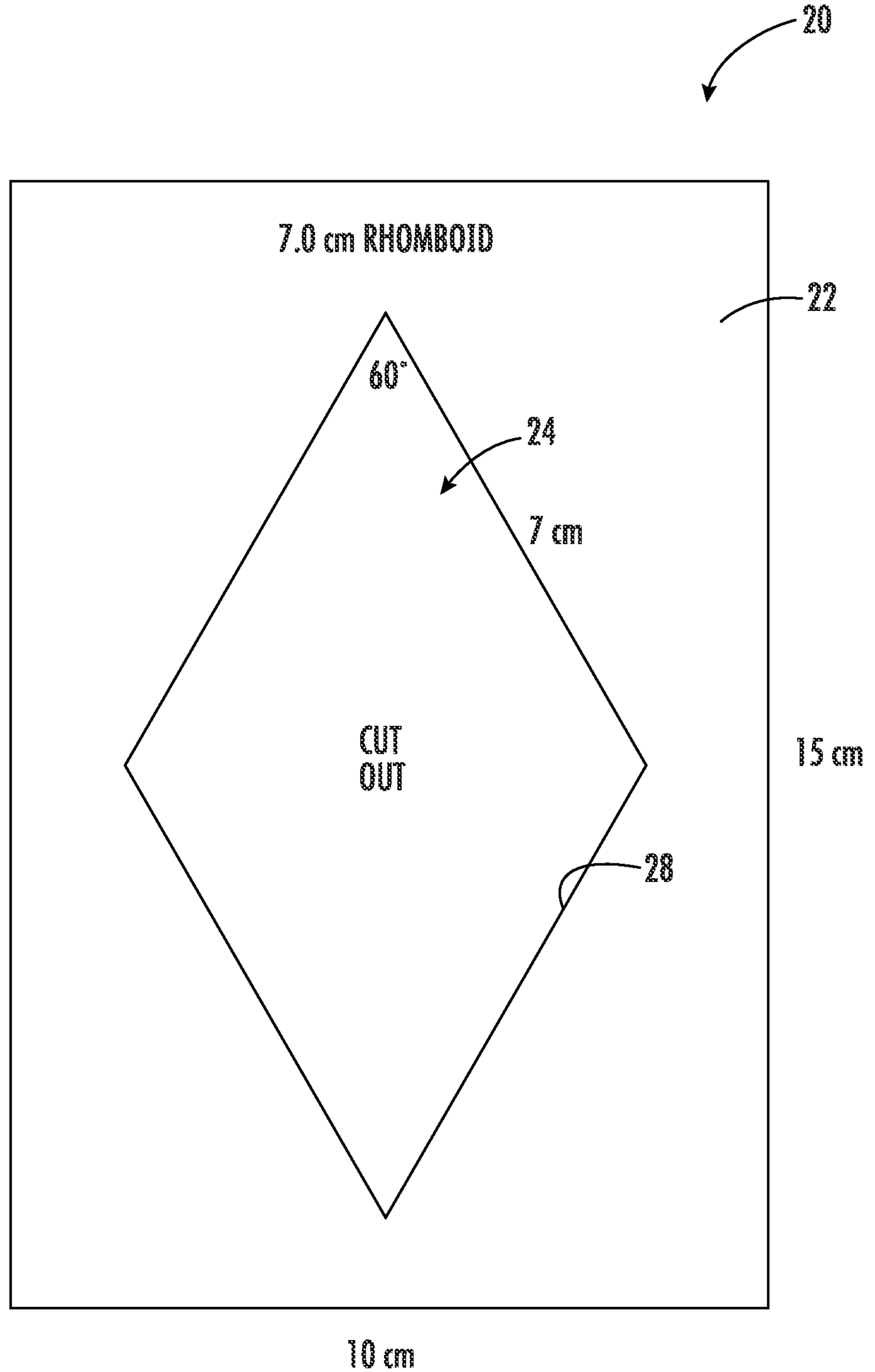
FIG. 11A is a top plan view of an embodiment of a first template having a rhomboid pattern for designing a skin flap for closure of a 7.0 cm wound opening or skin defect.
Figure 11B:
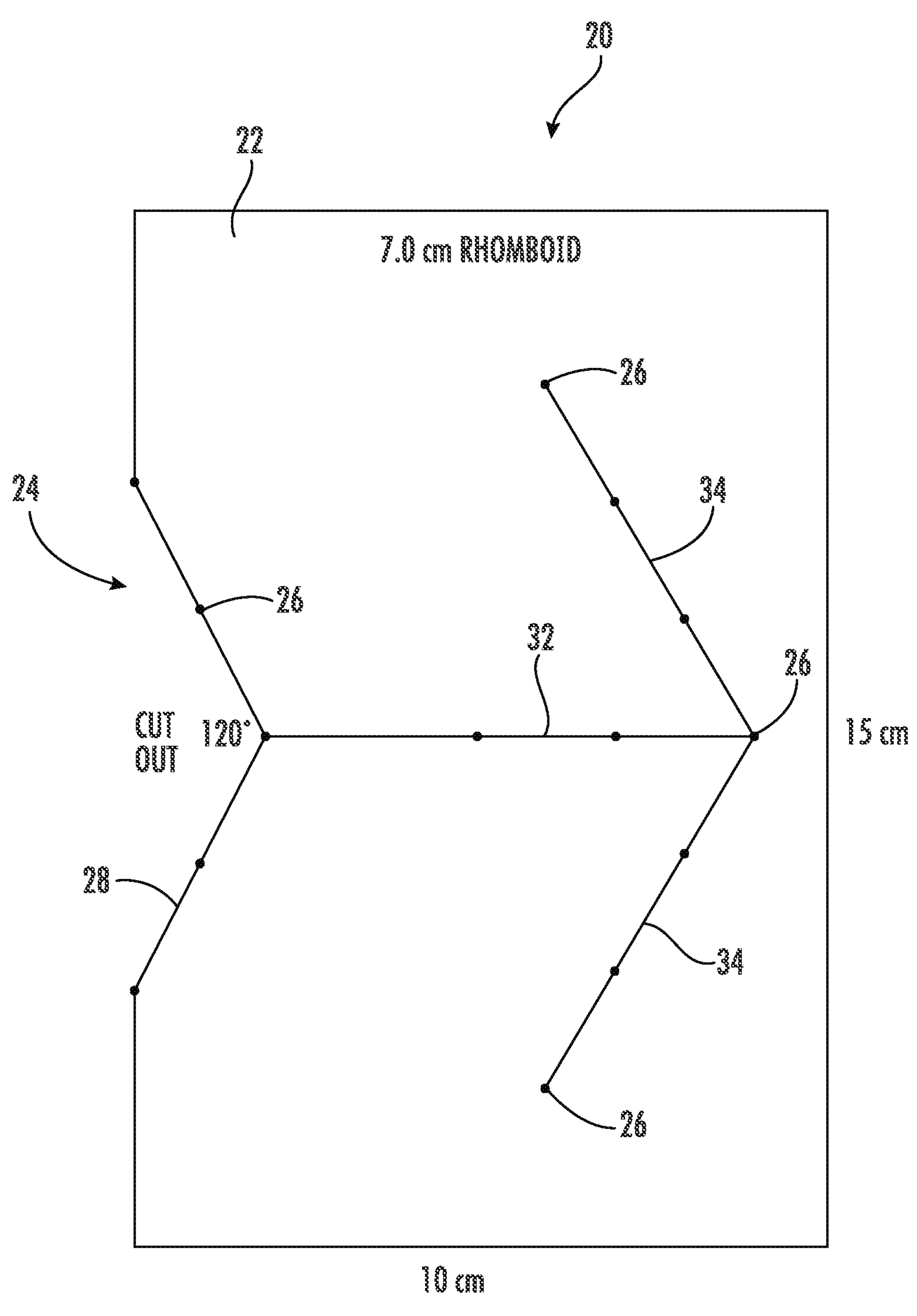
FIG. 11B is a top plan view of an embodiment of a second template having a rhomboid pattern for designing a skin flap for closure of a 7.0 cm wound opening or skin defect.
Figure 12A:
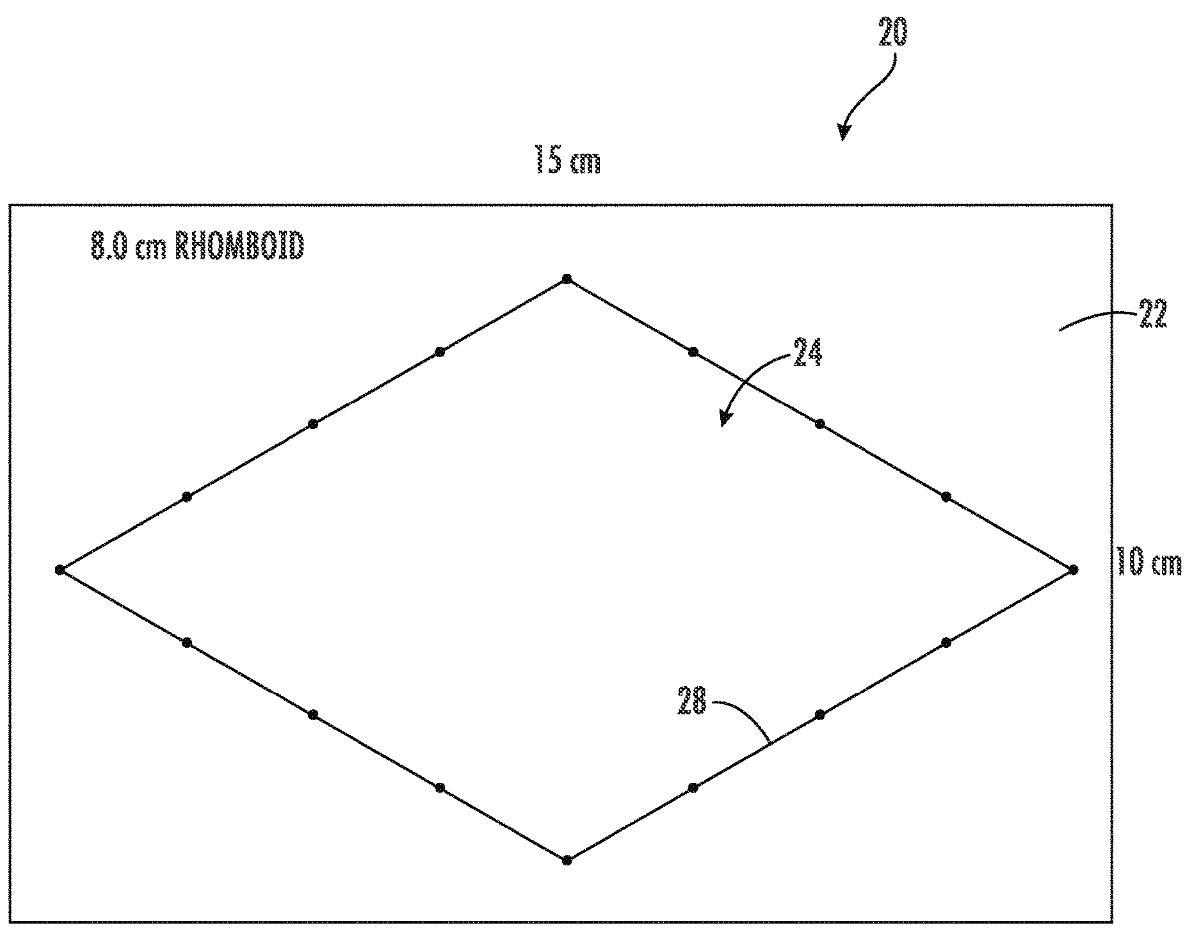
FIG. 12A is a top plan view of an embodiment of a first template having a rhomboid pattern for designing a skin flap for closure of an 8.0 cm wound opening or skin defect.
Figure 12B:
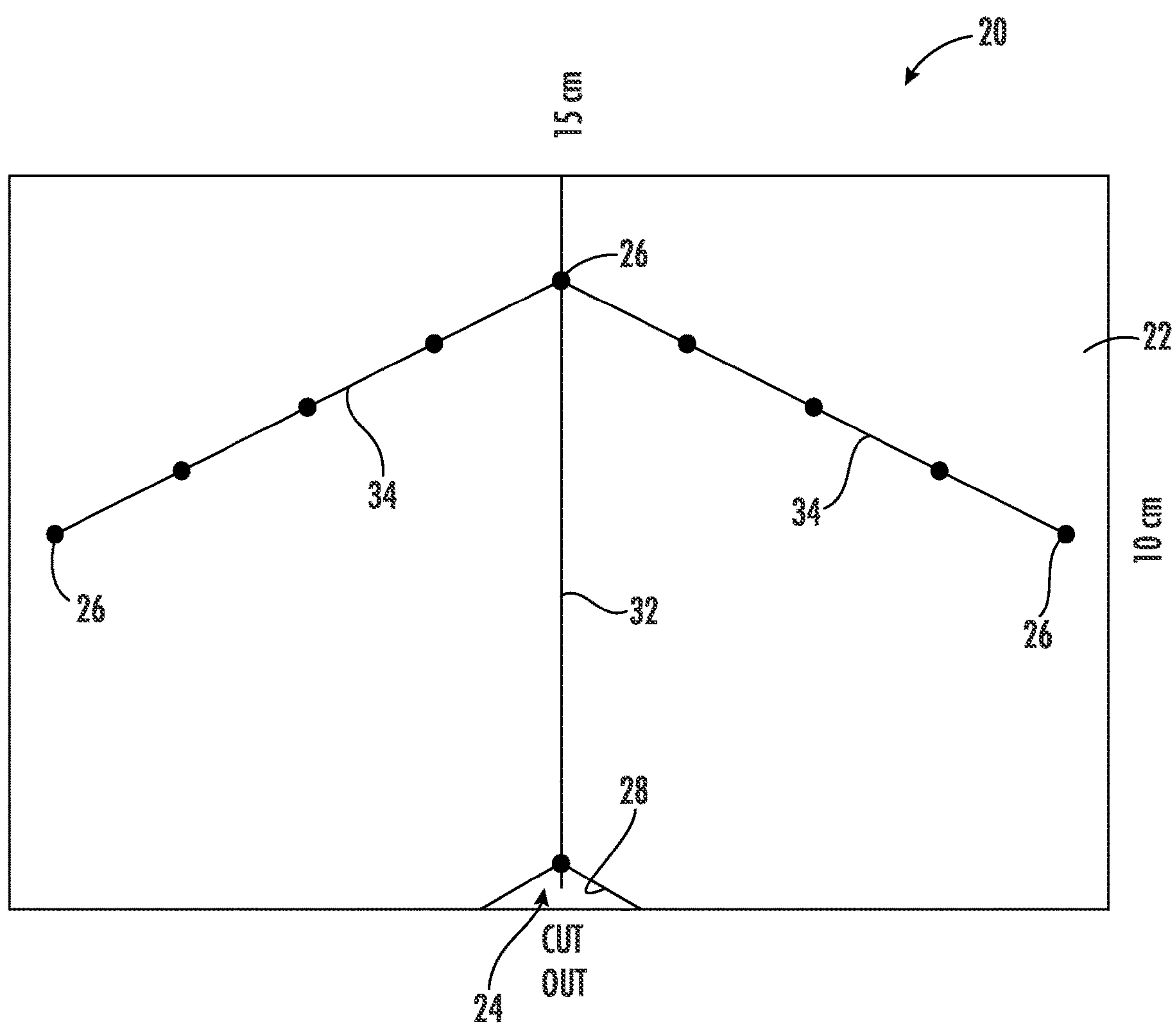
FIG. 12B is a top plan view of an embodiment of a second template having a rhomboid pattern for designing a skin flap for closure of a 8.0 cm wound opening or skin defect.
Figure 13:
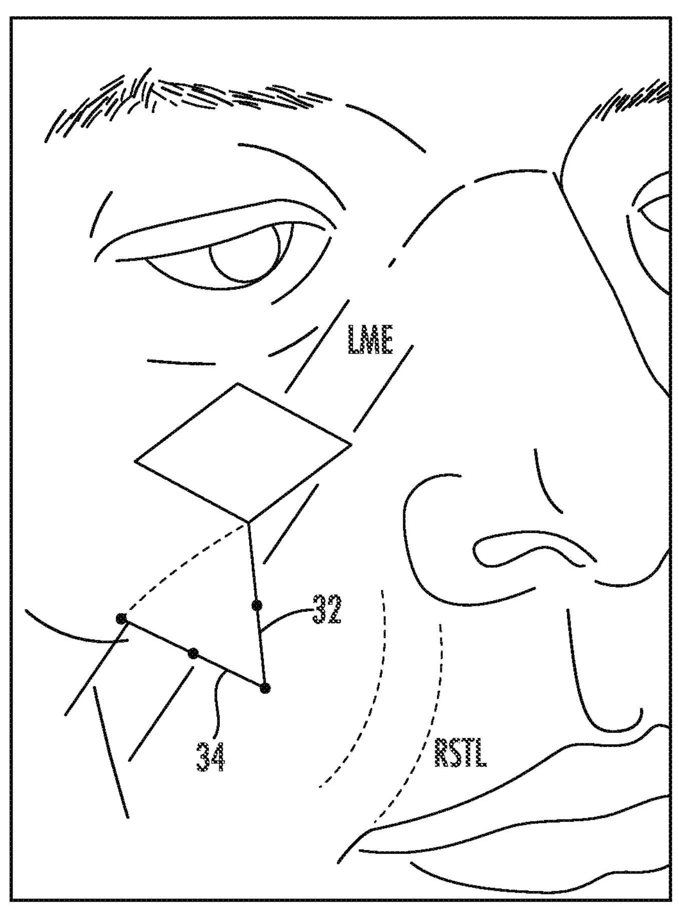
FIG. 13 is a side perspective view of a selected rhomboid pattern on a patient as shown in FIGS. 3-12*b* with two sides of the rhomboid flap and short diagonal parallel to the LME and perpendicular to the RSTL.
Figure 14A:
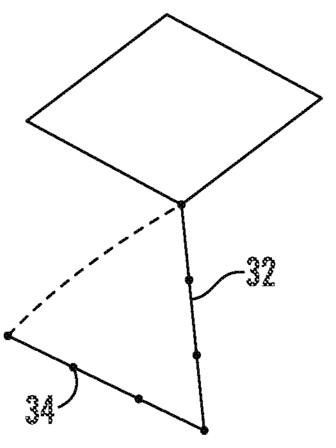
FIGS. 14A and 14B are top plan views of a rhomboid flap design to the skin and a vertical closure of the flap donor site, respectively.
Figure 14B:
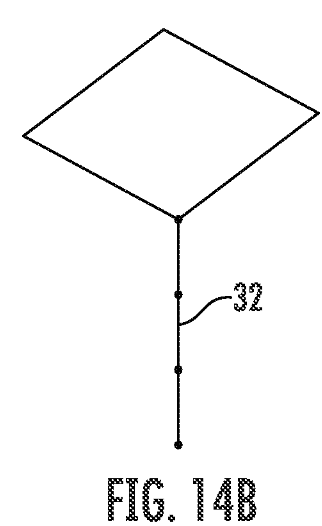

Two incision lines 32, 34 are required for creating the skin flap in the rhomboid procedure, a first line 32 extending from a corner of the rhomboid having a 120 degree angle and a second terminal incision line 34 extending at a 60 degree angle from the distal end of the first incision line 32. As seen, for example, in FIG. 3, the rhomboid pattern has optional holes 26 extending through the sheet material 22 at each of two of the opposed angles. These holes allow marking a proximal end of the first incision line 32. Another hole 26 spaced from the rhomboid pattern marks a common termination of each of the first and second lines 32, 34. A mark on the skin at this perforation 26 indicates a distal termination of the first line 32, as seen by the dot in FIG. 13, and a proximal end of the second incision line 34. The incision lines 32, 34 may be marked with a skin marker through the perforations 26 beginning at an appropriate corner of the rhomboid. Each mark on the skin is a dot and connecting the dots will provide the two linear incision lines 32, 34 generally extending from the rhomboid pattern 24. At a minimum, there should be a first dot at the intersection of the lines 32, 34 and a second dot at the distal end of the second line 34. The first incision line 32 from the corner of the rhomboid to the first dot is the same length as each of the sides of the rhomboid. The angular terminal second incision line 34 is the same length as the rhomboid sides. Likewise, the distance of the short diagonal is the same as the side of the rhomboid.

The sheet 22 of the template 20 is preferably formed of a pliable transparent material that may be readily made to conform to the contour surfaces of the skin prior to and during surgery when subjected to the forces of manual manipulation for placing and adjusting the template on the skin. Ideally, the template 20 may be repeatedly manipulated without being easily damaged and, after such activities, will generally maintain its shape. In one embodiment, the template 20 is constructed of, for example, a transparent acrylic that can be sterilized and packaged. Following use, the template can be re-sterilized and repackaged or used without sterilization in an outpatient environment. The material may be cleaned, disinfected, or sterilized between uses by art recognized methods such as, but not limited to, the use of detergents, alcohol, or autoclaving. The sheet material 22 preferably withstands repeated cleansing, disinfection, sterilization, or any combination thereof without significant deterioration. Additionally, the surface of the template 20 may be smooth, relatively smooth, or they may be textured, for instance, to prevent the template from slipping once positioned against the skin. Additionally, the sheet material 22 is preferably non-allergenic because of its use against the surface of the skin. Examples of suitable materials for the sheet material 22 of the template 20 include elastomers, such as silicone, polytetrafluoroethylene (PTFE), rubber, polyurethane, and other polymers with or without reinforcing materials such as dacron mesh. Ideally the material is transparent as described hereinabove.

The template 20 may be provided with various rhomboid flap dimensions to close wounds or skin openings of different sizes. This arrangement allows the surgeon to select the most suitable size for the rhomboid flap design. A plurality of templates 20 is shown in FIGS. 3-12B. Each template 20 is rectangular, measuring about 10 cm in length and about 5 cm in width. The rhomboid-shaped openings shown in the drawings range in sizes from about 1.0 cm to about 8 cm for wound diameters of up to 8.0 cm. The single templates having rhomboid sizes of 1.0 cm, 1.5 cm, 2.0 cm, 2.5 cm, 3.0 cm, 3.5 cm, 4.0 cm, 4.5 cm and 5.0 cm and are shown in FIGS. 3-9. Each template 20 provides selection of four rhomboid flap designs, two on one side and two on the other. Larger rhomboid sizes from about 6.0 cm to about 8.0 cm require two templates 20 for design of the rhomboid and the flap. Reversing the larger size templates 20 also provides four rhomboid flap designs, two when the template is placed on one corner having a 120 degree angle and two when placed on the other corner having the 120 degree angle.

In use, a surgeon first determines the size of a wound or skin defect and the excisions to be made for creating a skin opening or removing the defect. A surgical template 20 for a rhomboid flap procedure is selected based on the appropriate size of the excision relative to the wound or skin defect. The template 20 size may be determined by factors such as for example, but not limited to, how much skin is to be resected during the surgery. The template 20 is placed on the skin at the surgical site such that the wound or skin defect is exposed through the rhomboid opening 24. Due to the pliable nature of the sheet material 22, the template 20 may be further smoothed, pressed, or otherwise formed in curvature and shape so that it conforms to the skin. Optionally, the template 20 may also be secured to the skin to maintain its position. Means of securing the template include any recognized method such as taping, tacking, gluing or other adhesive, etc.

The template 20 is positioned to orientate the skin flap relative to the hole that will be created by the excision for the most desirable flap position. Template 20 placement is determined by first identifying the line of maximum extensibility (LME) of the skin. The surgeon will then place the template 20 with the wound or defect centered within the closed rhomboid figure to a desirable position relative to the LME. Placement of the rhomboid pattern requires two sides of the rhomboid pattern be parallel to the LME. Appropriate flap selection requires that the short diagonal of the flap must also be parallel to the LME. The surgeon will also determine if the selected flap will alter facial landmarks such as nose, hairlines or eyebrows and the like. The relaxed skin tension line (RSTL) and the vector of tension (VOT), which anticipates distortion of adjacent tissues are considered. Other considerations influencing flap selection include any existing scarring and laxity.

Once the surgeon has determined the orientation of the template 20, the surgeon uses the template 20 to mark the outline of the incision of the rhomboid by drawing lines. The skin marker is guided along the edges 28 of the rhomboid pattern, and the generally linear pattern of the edges are used to trace the rhomboid-shaped incision pattern on the skin. The surgeon will choose at least one of the four flap options for the incision lines 32, 34 corresponding to the selected rhomboid size. The selected incision lines 32, 34 may be marked on the skin with dots on the skin through the holes 26 to identify where each incision line 32, 34 will be made to produce the flap that will be used to cover the defect in the skin caused by the removal of the lesion or based on the size of the wound. Any number of art recognized, preferably sterile, marking devices may be used and in a preferred method the marking device is a permanent marker such as a Sharpie® pen or marker. For large wound or defect diameters requiring two templates 20, the template having the rhomboid pattern is used first followed by the template for the flap design. The latter has a notch for aligning with the selected 120 degree angle rhomboid corner. The preferred flap is then selected from the two flap designs represented two different terminal incision lines 34 extending in opposite directions. It is understood that by placing the flap template on the other 120 degree angle corner, two additional flap designs are available for selection. As noted above, the selected flap design should have two sides of the rhomboid and the short diagonal parallel to the LME.

Once the marking is complete, the template 20 is then set aside and surgery proceeds. The area within the rhomboid pattern is excised. The selected flap is elevated and transferred to cover the defect. Alternatively, the surgeon can excise the skin with the template 20 in place and then remove the template to incise the incision lines 32, 34 for the flap. In either case, skin tissue is excised leaving a rhomboid shaped hole in the skin. Incision lines 32, 34 form the flap 20. The flap is then moved into position over the defect for suturing. It is understood that the portion of the flap which will cover the hole will be moved. Therefore, it is necessary that the skin at the flap and some surrounding skin be free from the flesh beneath it. This will typically require the skin to be undercut so that it is free to move.

The surgical template described herein and its use for preparing a rhomboid pattern and flap for skin closure of difficult wounds has many advantages, including providing ease and rapidity of use. Complicated operative and pre-operative planning is facilitated. Utilization is available to surgeons of varying disciplines. Operative time and associated costs are significantly reduced. The plurality of templates 20 offer a selection of sizes from 1.0 cm to 8.0 cm having one pattern with one size corresponding to flap coverage. Different surgical specialties requiring wound closure are provided varying sizes for their use.

It is understood that the template may be provided in a single unit in a sterilized package or a plurality of templates of the same or different sizes may be packaged together in a kit. The templates can be pre-sterilized before packaging. The template 20 can also be used or re-used when not sterile in the pre-op or outpatient setting.

I claim:

1. A surgical template for marking a pattern on skin prior to performing surgery to create a skin flap for closing an opening or wound on the skin, the template comprising a substantially planar sheet having an opening defined by a continuous edge forming a closed geometric figure in substantially the shape of a rhomboid, the sheet having all sides equal a first pair of holes linearly spaced along an axis passing through opposed obtuse corners of the rhomboid such that the distance between one of the obtuse corners of the rhomboid and the adjacent hole of the first pair of holes is equal to the length of the sides of the rhomboid, and a second pair and a third pair of holes, each hole of the second pair and the third pair of holes spaced from the first pair of holes such that a line from the adjacent hole of the first pair of holes to the adjacent one of the second pair or third pair of holes is parallel to and equal in length to the adjacent side of the rhomboid, and the surgical template capable of being at least one of smoothed, pressed, and formed in curvature and shape to conform the surgical template to the skin, wherein placement of the surgical template allows orientation of the skin flap such that it avoids distortion of an adjacent tissue, wherein the edges of the sheet defining the opening form a border for mechanically guiding a marker for marking excision lines on the skin surrounding the portion of skin intended to be removed, and wherein each of the pairs of holes define linear axes therebetween for marking incision lines on the skin forming a pattern for the skin flap.

2. The surgical template as recited in claim 1, wherein the sheet comprises a flexible, transparent material to conform the surgical template to the skin.

3. The surgical template as recited in claim 1, wherein the edges of the sheet defining the opening are configured for receiving at least a portion of a cutting edge of an incising instrument and for guiding the incising instrument during an incising of the skin.

4. The surgical template as recited in claim 2, wherein when the surgical template conforms to the skin, the surgical template becomes secured to the skin to maintain a position of the surgical template.

5. A method for marking a pattern on skin prior to performing surgery to create a skin flap for closing an opening or wound in the skin, the skin pattern marking method comprising the steps of:

providing a substantially planar sheet having an opening defining a closed geometric figure in substantially the shape of a rhomboid, the sheet having a first pair of holes linearly spaced along an axis passing through opposed obtuse corners of the rhomboid such that the distance between one of the obtuse corners of the rhomboid and the adjacent hole of the first pair of holes is equal to the length of the sides of the rhomboid, and a second pair and a third pair of holes, each hole of the second pair and the third pair of holes spaced from the first pair of holes such that a line from the adjacent hole of the first pair of holes to the adjacent one of the second pair or third pair of holes is parallel to and equal in length to the adjacent side of the rhomboid;

at least one of smoothing, pressing, and forming in curvature and shape to conform a position of the sheet on the skin;

marking the skin along the edges of the sheet defining the opening transferring the rhomboid pattern to the skin for use as excision lines for skin removal forming a hole in the skin flap by drawing a linear incision line extending from the adjacent corner of the rhomboid opening and between the dots representing the incision to be made in the skin to produce the flap;

excising following the lines of the closed geometric figure marking for removing skin making a hole to be closed; and making an incision in the skin along the lines between the dots to produce a local flap to cover the hole in the skin wherein placement of the surgical template allows orientation of the skin flap such that it avoids distortion of an adjacent tissue.

6. The skin pattern marking method as recited in claim 5, further comprising the step of selecting a predetermined opening size from among a plurality of templates having different sizes of rhomboid-shaped openings.

7. The skin pattern marking method as recited in claim 5, further comprising the step of selecting the orientation of the flap by rotating the template on the skin.

8. The skin pattern marking method as recited in claim 7, wherein the step of selecting the orientation of the flap comprises:

identifying the line of maximum extensibility (LME) of the skin, aligning the template such that two sides of the rhomboid pattern are parallel to the LME, and aligning a short linear diagonal of the flap extending between the corner of the rhomboid and the adjacent hole of the second or third pair of holes parallel to the LME.

9. The skin pattern marking method as recited in claim 7, wherein the step of selecting the orientation of the flap comprises consideration of the relaxed tension line (RSTL) and the vector version of tension (VOT) for anticipating distortion of adjacent tissues.

10. The skin pattern marking method as recited in claim 5, further comprising the steps of cutting through the skin along the excision lines and removing the patch of skin of rhomboid shape.

* * * * *